(12) United States Patent
Fritsche et al.

(10) Patent No.: US 9,546,983 B2
(45) Date of Patent: Jan. 17, 2017

(54) GAS BUBBLE SENSING DEVICE WITH TWO ULTRASONIC EMITTERS CONNECTED TO ONE ULTRASONIC SIGNAL GENERATOR

(71) Applicant: SONOTEC Ultraschallsensorik Halle GmbH, Halle/Saale (DE)

(72) Inventors: Tobias Fritsche, Halle/Saale (DE); Santer Zur Horst-Meyer, Halle/Saale (DE); Hans-Joachim Münch, Halle/Saale (DE)

(73) Assignee: Sonotec Ultraschallsensorik Halle GmbH, Saale (DE)

( * ) Notice: Subject to any disclaimer, the term of this patent is extended or adjusted under 35 U.S.C. 154(b) by 318 days.

(21) Appl. No.: 14/300,675

(22) Filed: Jun. 10, 2014

(65) Prior Publication Data

US 2014/0360248 A1    Dec. 11, 2014

Related U.S. Application Data

(60) Provisional application No. 61/833,692, filed on Jun. 11, 2013.

(51) Int. Cl.
*G01N 29/02* (2006.01)
*G08B 21/18* (2006.01)
*G01N 29/34* (2006.01)
*G01N 29/024* (2006.01)

(52) U.S. Cl.
CPC ............ *G01N 29/02* (2013.01); *G01N 29/024* (2013.01); *G01N 29/348* (2013.01); *G08B 21/18* (2013.01); *G01N 2291/02433* (2013.01); *G01N 2291/02466* (2013.01)

(58) Field of Classification Search
CPC ........ A61B 8/06; G01N 29/02; G01N 29/348; G01N 2291/02433; G01N 2291/02466; G08B 21/18

USPC ................................................ 73/19.03, 19.1
See application file for complete search history.

(56) References Cited

U.S. PATENT DOCUMENTS

| 4,557,148 A | * | 12/1985 | Akiyama | ................ G01F 1/667 |
| | | | | 702/48 |
| 4,567,749 A | * | 2/1986 | Amblard | ................ G01N 15/02 |
| | | | | 73/19.03 |
| 7,694,565 B2 | * | 4/2010 | Koerdt | ..................... A61B 8/06 |
| | | | | 73/597 |

FOREIGN PATENT DOCUMENTS

GB    1578660    * 11/1980

* cited by examiner

*Primary Examiner* — Daniel S Larkin
(74) *Attorney, Agent, or Firm* — Norris McLaughlin & Marcus, P.A.

(57) ABSTRACT

The invention relates to a gas bubble sensing device (1) for sensing gas bubbles in a liquid. In order to provide a reliable detection of inadmissible gas bubbles at minimum cost and required installation space, the invention provides that the gas bubble sensing device (1) comprises two ultrasonic emitters (2, 3), which are both connected to one ultrasonic signal generator (10) in a signal transmitting manner.

A gas bubble sensing device senses gas bubbles in a liquid. The gas bubble sensing device comprises two ultrasonic emitters, which are both connected to one ultrasonic signal generator in a signal transmitting manner. Further, the gas bubble sensing device comprises two control devices that are each connected to one of the signal processing devices in a signal transmitting manner, wherein one of the control devices comprises an output port, at which it provides a synchronization signal during operation.

11 Claims, 1 Drawing Sheet

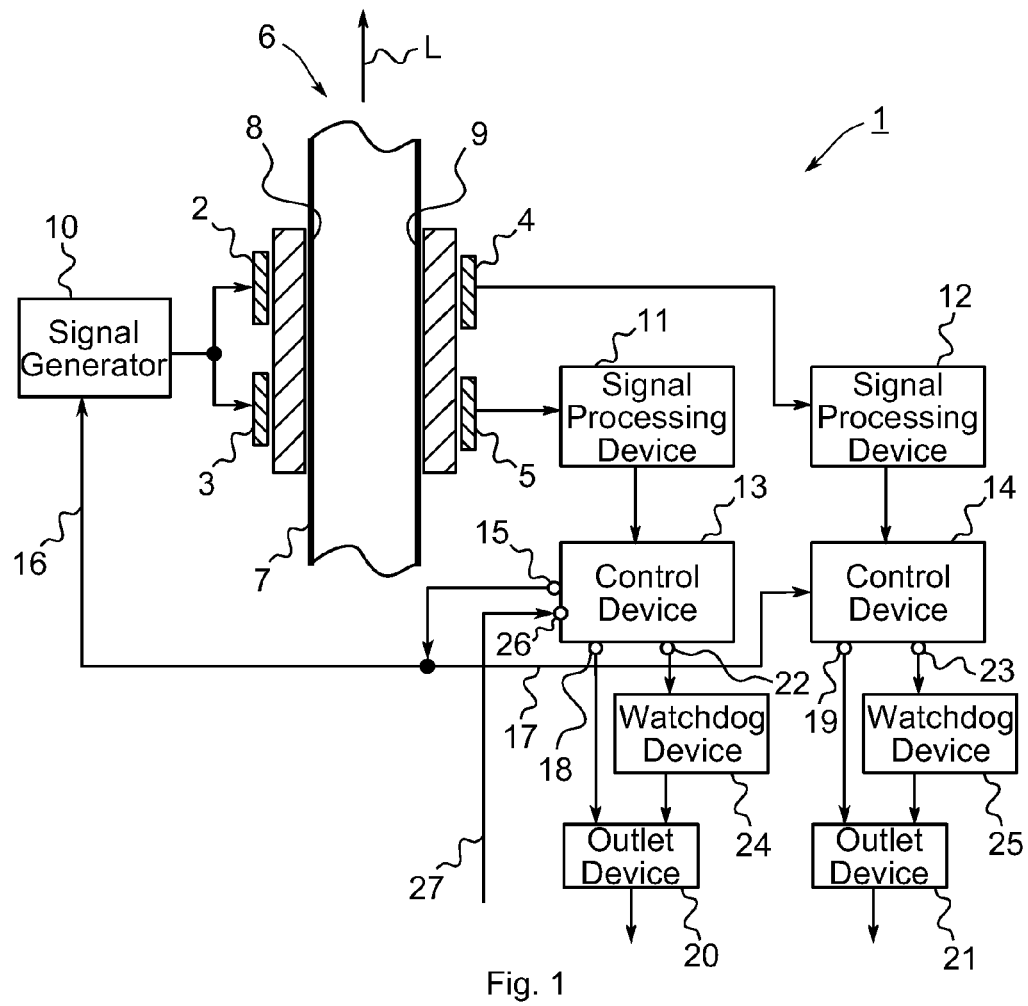
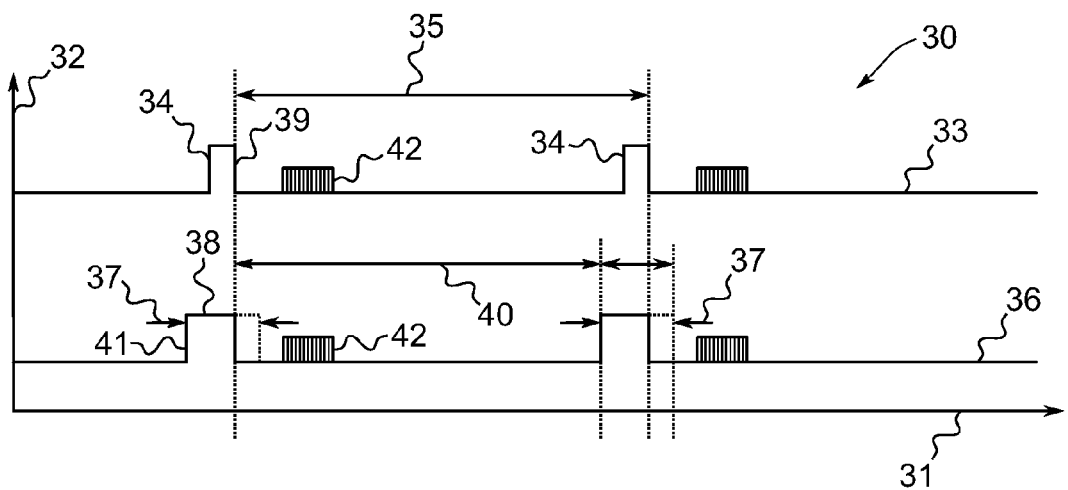

GAS BUBBLE SENSING DEVICE WITH TWO ULTRASONIC EMITTERS CONNECTED TO ONE ULTRASONIC SIGNAL GENERATOR

TECHNICAL FIELD OF THE DISCLOSURE

The invention relates to gas bubble sensing device for sensing gas bubbles in a liquid, with a flow through channel for a liquid, two ultrasonic emitters and two ultrasonic receivers, wherein the emitters are each arranged opposite of a respective other one of the receivers with respect to the flow through channel, and with two signal processing devices, each of which being connected to one of the receivers in a signal transmitting manner.

Gas bubble sensing devices for sensing gas bubbles in a liquid are known in the art. For instance, known gas bubble sensing devices are used in intensive-care medicine in order to assure that blood transported by a life support machine and returned to a patient is free of inadmissible gas bubbles, which would be life threatening for the patient. Furthermore, the gas bubble sensing devices known in the art are used for monitoring that no inadmissible gas bubbles are transported with a liquid that shall be dispensed, for instance liquid adhesives or other liquids.

In order to reliably detect gas bubbles, known gas bubble sensing devices are redundantly constructed. A redundant construction, however, is cost intensive and requires a large installation space, which is often limited. In particular, in case the gas bubble sensing device is a clamp on sensor, which can be clamped onto a tube transporting liquid, e.g. blood, installation space is limited. Furthermore, redundant sensors are heavy, such that clamping forces may not be sufficient to hold the gas bubble sensing device on the tube.

SUMMARY OF THE DISCLOSURE

Thus, it is an object of the invention to provide a gas bubble sensing device with which gas bubbles can be reliably detected, wherein the gas bubble sensing device has a simple structure and requires a small installation space.

For the gas bubble sensing device mentioned above, the object is achieved in that the gas bubble sensing device comprises an ultrasonic signal generator that is connected to both of the emitters in a signal transmitting manner. In particular, the gas bubble sensing device may comprise only one ultrasonic signal generator. Further, the gas bubble sensing device comprises two control devices that are each connected to a respective other one of the signal processing devices in a signal transmitting manner, wherein one of the control devices comprises an output port, at which it provides a synchronization signal during operation.

In contrast to a redundant construction, which would comprise two ultrasonic signal generators, each of which being connected to one of the emitters in a signal transmitting manner, the gas bubble sensing device according to the invention requires a smaller installation space, as it only comprises one ultrasonic signal generator, which is connected to both of the emitters. Still, omitting one of the ultrasonic signal generators from the redundant gas bubble sensing device does neither impair the reliability of the measurement of the gas bubble sensing device, nor makes it a diagnostic of the gas bubble sensing device more complicated. Rather, the gas bubble sensing device according to the invention provides for the same operation safety and possibilities for trouble shooting as the redundant gas bubble sensing device, whereas it requires a smaller installation space and is lighter than the redundant gas bubbling sensing device.

The solutions according to the invention can be combined as desired and further improved by the further following embodiments that are advantages on their own, in each case and if not stated to the contrary.

According to a first possible embodiment, the emitters may be arranged on one side and the receivers may be arranged on another side opposite of the one side of the flow through channel. Arranging both emitters on one side and both receivers on the opposite side of the flow through channel reduces wiring of the emitters and the receivers. Furthermore, crosstalk is reduced compared to arrangements, in which one of the emitters is arranged on the one side and the other one of the emitters is arranged on the opposite side and the receivers are each arranged opposite of one of the emitters.

The gas bubble sensing device may comprise two control devices that are each connected to one of the signal processing devices in a signal transmitting manner, wherein one of the control devices comprises an output port, at which it provides a synchronization signal during operation. Based on the synchronization signal, other elements of the gas bubble sensing device may be operated in a synchronized manner, such that malfunctions of the gas bubble sensing device can be detected more easily, for instance by detecting if a signal is received within a predetermined time period after the synchronization signal.

For instance, the output port may be connected to the ultrasonic signal generator in a synchronization signal transmitting manner. Hence, the ultrasonic signal generator can be operated dependent on the synchronization signal.

In particular, the ultrasonic signal generator can be adapted to emit an ultrasonic signal pulse or an ultrasonic signal pulse train based on the synchronization signal. The ultrasound pulse or the ultrasound pulse train may have a frequency of about 2 MHz. An interval between two consecutive pulses or pulse trains can be defined by the synchronization signal such that useful signals can be distinguished from not useful signals, e.g. reflections from a previous ultrasound pulse or ultrasound pulse train.

One of the control devices may be adapted to output a fault signal in case an ultrasound pulse or ultrasound pulse train is not received within a predetermined time period. In particular, the fault signal is output, if the ultrasound pulse or pulse train is not received within a predetermined time period after the synchronization signal is output or received. It may be the control device that provides the synchronization signal that is adapted to monitor the receipt of the ultrasound signal and to output the fault signal if necessary.

Therefore, the control device that is adapted to output the fault signal in case the ultrasound pulse is not received within a predetermined time period monitors the functional state of the ultrasound emitters and for instance also of the ultrasonic signal generator. Additionally, the functional state of the receiver connected to this control device is monitored.

However, according to an advantageous embodiment, both of the control devices are adapted to monitor the receipt of ultrasound pulses within the predetermined time period and to output a fault signal in case the ultrasound pulse is not received within the predetermined time. In order to enable both of the control devices to monitor the receipt of the ultrasound pulses and to output a fault signal, the output port is preferably connected to the other one of the control devices in a synchronization signal transmitting manner.

Therefore, alternatively or additionally, the other one of the control devices may be adapted to output a fault signal in case an ultrasound pulse is not received within a predetermined time period, e.g. after the synchronization signal is received.

Hence, not only can the functional state of the ultrasound emitters and for instance also of the ultrasonic signal be generator monitored. Additionally, it can be distinguished which of the receivers is operative or nor.

Furthermore, the other one of the control devices may be adapted to output a fault signal in case the synchronization signal is not received within a predetermined time period. Hence, the other one of the control devices can monitor the functional state of the one of the control devices that provides for the synchronization signal.

The fault signal may differ from a gas bubble alarm signal, in order to distinguish a malfunction of the gas bubble sensing device from an inadmissible gas bubble. In case distinguishing a malfunction from an inadmissible gas bubble is not necessary, the fault signal preferably corresponds to the gas bubble alarm signal, in order to provide a straight forward fault and alarm signal processing.

The gas bubble sensing device may comprise two watchdog devices for monitoring the functional capability of the two control devices. Thus, in case one of the control devices has a malfunction and cannot output the fault signal, the watchdog devices can provide a fault signal or even the fault signal.

Furthermore, the gas bubble sensing device may comprise two voltage control devices for monitoring power supplies for the signal processing devices or for monitoring signal voltages of output signals output from the two control devices, thereby redundantly with the watchdog devices monitoring the control devices.

The invention is described hereinafter in greater detail and in an exemplary manner using advantageous embodiments and with reference to the drawings. The described embodiments are only possible configurations, in which, however, the individual features as described above can be provided or combined independently of one another or can be omitted in the drawings, unless stated otherwise:

BRIEF DESCRIPTION OF THE DRAWING FIGURES

FIG. 1 shows an exemplary embodiment of the gas bubble sensing device according to the invention in a cross-sectional view; and FIG. 2 shows a signal flow diagram.

DETAILED DESCRIPTION OF THE PREFERRED EMBODIMENTS

FIG. 1 shows a gas bubble sensing device 1 in a schematic cross-sectional view, sectioned along a longitudinal direction L according to a possible embodiment of the invention. The gas bubble sensing device 1 comprises two ultrasonic emitters 2, 3 and two ultrasonic receivers 4, 5. The emitters 2, 3 are ranged on one side and the receivers 4, 5 on another side of a flow through channel 6 of the gas bubble sensing device 1, the flow through channel 6 extending along the longitudinal direction L between the emitters 2, 3 and the receivers 4, 5. Through the flow through channel 6, a liquid may flow in the longitudinal direction L. In FIG. 1, however, a flexible tube 7 is arranged in the flow through channel 6, through which a liquid that shall be checked for gas bubbles may flow along the longitudinal direction L. In the flow through channel 6, the tube 7 may be held due to elastic deformation of the tube 7, such that the tube 7 rests against side walls 8, 9 of the flow through channel 6. Sidewall 8 is arranged between the emitters 2, 3 and the flow through channel 6 and sidewall 9 is arranged between the receivers 4, 5 and the flow through channel 6.

During operation of the gas bubble sensing device 1, the emitters 2, 3 emit ultrasound, which is conducted via the sidewall 8 and through the flow through channel 6 to the sidewall 9 and to the receivers 4, 5. The receivers 4, 5 provide a measurement signal based on the ultrasound. A gas bubble free liquid conducts the ultrasound better than a liquid with gas bubbles or than the gas alone. The measurement signals, which are converted by the receivers 4, 5 based on the ultrasound received, represent the presence and the size of gas bubbles in the liquid or whether liquid is present in the flow through channel 6 or not.

According to the exemplary embodiment of FIG. 1, the gas bubble sensing device 1 comprises one ultrasonic signal generator 10, which provides an ultrasound signal to both of the emitters 2, 3. In order to provide the ultrasound signal to the emitters 2, 3, the ultrasonic signal generator 10 is connected to each of the emitters 2, 3 in a signal transmitting manner.

Each of the receivers 4, 5 is connected to one signal processing device 11, 12. The signal processing devices 11, 12 are each connected to one of the receivers 4, 5 in a signal transmitting manner in order to receive the measurement signal provided by the receivers 4, 5. The signal processing devices 11, 12 may comprise a measurement signal amplifier, a signal peak detector and/or an analog to digital converter. Both of the signal processing devices 11, 12 output a processed measurement signal to a control device 13, 14. Hence, each of the control devices 13, 14 is connected to one of the signal processing devices 11, 12 in a signal transmitting manner.

Control device 13 comprises an output port 15, via which the control device 13 can provide a synchronization signal during operation of the gas bubble sensing device 1. For instance, the ultrasonic signal generator 10 can be connected to the output port 15 in a synchronization signal transmitting manner, such that the ultrasonic signal generator 10 can emit ultrasound in dependence of the synchronization signal. In particular, the ultrasonic signal generator can emit an ultrasound pulse or pulse trains upon receipt of the synchronization signal, which may for instance be a pulsed or periodic synchronization signal. According to the exemplary embodiment of FIG. 1, a synchronization signal conductor 16 interconnects the output port 15 and the ultrasonic signal generator 10.

Optionally or additionally, a synchronization signal conductor 17 may interconnect the output port 15 and the other control device 14 in order to provide the synchronization signal to the control device 14. Preferably, the synchronization signal is provided to both, the ultrasonic signal generator 10 and the control device 14. The control device 13, which provides the synchronization signal, may be designated as synchronization master. The ultrasonic signal generator 10 and/or the control device 14, which receive the synchronization signal, may be designated as synchronization slaves.

Each of the control devices 13, 14 comprises a status output port 18, 19 for outputting a status signal representative of the condition of the gas bubble sensing device 1 or for gas bubbles inside the liquid. For instance, the status signal may represent a fault of a component of the gas bubble sensing device 1 or a gas alarm, in case an inadmissible gas bubble passes through the flow through channel 6 and along the emitters 2, 3 and the receivers 4, 5. The status signal is output from the status output ports 18, 19 to outlet devices 20, 21 for connecting the gas bubble sensing device 1 to an external device, for instance to a life support machine or a machine for transporting or dispensing other liquids.

Furthermore, according to the exemplary embodiment of FIG. 1, both of the control devices 13, 14 may be equipped with a monitoring port 22, 23. In order to monitor the status of the control devices 13, 14, the gas bubble sensing device 1 according to the exemplary embodiment is equipped with watchdog devices 24, 25. Each of the watchdog devices 24, 25 is connected to one of the monitoring ports 22, 23 and monitors the condition of the respective control device 13, 14 and for instance, if the control device 13, 14 is operative or not.

Alternatively or additionally to the watchdog devices 24, 25, the gas bubble sensing device 1 may comprise two voltage control devices for monitoring signal levels or the power supply of the signal processing devices 11, 12 and/or of the control devices 13, 14. The voltage control devices may be integrated into the watchdog devices 24, 25 or may be formed separately.

The watchdog devices 24, 25 and/or the voltage control devices may provide another fault signal or the fault signal to the outlet devices 20, 21.

In order to be able to test the operational availability of the gas bubble sensing device 1, control device 13 may comprise a test port 26, to which a test signal may be applied via a test line 27. Upon receipt of the test signal at the test port 26, the control device 13 may emit the synchronization signal or may omit the synchronization signal in order to provoke the generation of the fault signal.

FIG. 2 shows a signal flow diagram according to an exemplary embodiment of the invention, wherein among the signals shown is the synchronization signal.

The signal flow diagram 30 comprises an ordinate 31, which represents the lapse of time. An abscissa 32 of the diagram 30 represents signal levels with arbitrary units.

Signal 33 is the synchronization signal provided by control device 13. The synchronization signal 33 may comprise synchronization pulses 34, which are provided at predetermined intervals 35. For instance, the synchronization signal 33 may be a periodic signal.

Signal 36 is a monitoring signal, which may be present in a synchronization slave, for instance in the ultrasonic signal generator 10 and/or in the control device 14. Based on the monitoring signal 36, it can be checked whether a synchronization pulse 34 is received within an expected time window 37. The expected time window 37 is represented by a pulse 38, whose maximum width represents the length of the expected time window 37. In case a falling flank 39 of the synchronization pulse 34 is detected within the expected time window 37, the synchronization pulse 34 is deemed to be received in time and no fault signal is generated. In case the falling flank 39 is not received within the expected time window 37, the fault signal is generated.

Upon receipt of the falling flank 39 of the synchronization pulse 34, a wait interval 40 begins. At the end of the wait interval 40, another expected time window 37 opens. The wait interval 40 is shorter than the interval 35 between falling flanks 39 of subsequent synchronization pulses 34. In case the interval 35 is constant, a distance between rising flanks 41 of subsequent pulses 38 corresponds to the interval 35.

Between subsequent synchronization pulses 34, a processed measurement signal 42 that is for instance representative for an ultrasound pulse or an ultrasound pulse train comprising several ultrasound pulses, is received by the control devices 13 and 14. Processed measurement signals 42 received by the control device 13 are shown close to the synchronization signal 33. Processed measurement signals 42 received by the control device 14 are shown close to the monitoring signal 36.

Due to the synchronization signal 33, the ultrasound signals 42 are received by the control devices 13, 14 almost simultaneously. In case no processed measurement signals 42 are received by either or any of the control devices 13, 14, the fault signal is generated.

The invention claimed is:

1. A gas bubble sensing device for sensing gas bubbles in a liquid, with a flow through channel for a liquid, two ultrasonic emitters and two ultrasonic receivers, wherein the emitters are each arranged opposite of a respective other one of the receivers with respect to the flow through channel, and with two signal processing devices, each of which being connected to one of the receivers in a signal transmitting manner, further comprising an ultrasonic signal generator that is connected to both of the emitters in a signal transmitting manner, and two control devices that are each connected to a respective other one of the signal processing devices in a signal transmitting manner, wherein one of the control devices comprises an output port, at which it provides a synchronization signal during operation.

2. The gas bubble sensing device according to claim 1, wherein the emitters are arranged on one side and the receivers are arranged on another side opposite the one side of the flow through channel.

3. The gas bubble sensing device according to claim 1, wherein the output port is connected to the ultrasonic signal generator in a synchronization signal transmitting manner.

4. The gas bubble sensing device according to claim 1, wherein the ultrasonic signal generator is adapted to emit an ultrasonic signal pulse based on the synchronization signal.

5. The gas bubble sensing device according to claim 1, wherein one of the control devices is adapted to output a fault signal in case an ultrasound pulse is not received within a predetermined time period.

6. The gas bubble sensing device according to claim 5, wherein the fault signal corresponds to a gas bubble alarm signal.

7. The gas bubble sensing device according to claim 1, wherein the output port is connected to the other one of the control devices in a synchronization signal transmitting manner.

8. The gas bubble sensing device according to claim 7, wherein the other one of the control devices is adapted to output a fault signal in a case where the synchronization signal is not received within a predetermined time period.

9. The gas bubble sensing device according to claim 1, wherein the other one of the control devices is adapted to output a fault signal in a case where an ultrasound pulse is not received within a predetermined time.

10. The gas bubble sensing device according to claim 1, further comprising two watchdog devices for monitoring the functional capability of the two control devices.

11. The gas bubble sensing device according to claim 1, further comprising two voltage control devices for monitoring power supplies for the signal processing devices and/or the control devices.

* * * * *